US012582353B2

(12) United States Patent
Zeid et al.

(10) Patent No.: US 12,582,353 B2
(45) Date of Patent: Mar. 24, 2026

(54) EVALUATING DRUG EFFICACY BY USING WEARABLE SENSORS

(71) Applicant: Sanofi, Paris (FR)

(72) Inventors: Elias Abou Zeid, Methuen, MA (US); Hillol Sarker, Belmont, MA (US); Archana Vaithilingam, Waban, MA (US); Dina Vogt, Belle Mead, NJ (US)

(73) Assignee: Sanofi, Paris (FR)

( * ) Notice: Subject to any disclaimer, the term of this patent is extended or adjusted under 35 U.S.C. 154(b) by 671 days.

(21) Appl. No.: 17/899,194

(22) Filed: Aug. 30, 2022

(65) Prior Publication Data

US 2023/0068469 A1 Mar. 2, 2023

Related U.S. Application Data

(60) Provisional application No. 63/342,815, filed on May 17, 2022, provisional application No. 63/239,213, filed on Aug. 31, 2021.

(30) Foreign Application Priority Data

Nov. 5, 2021 (EP) .................................... 21315235

(51) Int. Cl.
| | |
|---|---|
| A61B 5/00 | (2006.01) |
| A61B 5/11 | (2006.01) |
| G16H 10/60 | (2018.01) |
| G16H 20/10 | (2018.01) |

(52) U.S. Cl.
CPC .......... *A61B 5/4848* (2013.01); *A61B 5/0022* (2013.01); *A61B 5/11* (2013.01); *A61B 5/4818* (2013.01); *A61B 5/6802* (2013.01); *A61B 5/7203* (2013.01); *G16H 10/60* (2018.01); *G16H 20/10* (2018.01)

(58) Field of Classification Search
None
See application file for complete search history.

(56) References Cited

U.S. PATENT DOCUMENTS

| | | | | |
|---|---|---|---|---|
| 9,773,308 | B2 | 9/2017 | Silbersweig et al. | |
| 10,264,971 | B1 * | 4/2019 | Kennedy .............. | A61B 5/6804 |
| 2011/0313261 | A1 * | 12/2011 | Bourget ............... | A61B 5/0031 |
| | | | | 600/382 |
| 2018/0070875 | A1 | 3/2018 | Kshetrapal | |
| 2022/0125386 | A1 * | 4/2022 | Marras .................. | A61B 5/1114 |

FOREIGN PATENT DOCUMENTS

| | | | | |
|---|---|---|---|---|
| EP | 1962686 | 11/2009 | | |
| WO | WO 2021/152551 | 8/2021 | | |
| WO | WO-2021152551 A1 * | 8/2021 | .............. | A61B 5/11 |
| WO | WO 2023/034267 A1 | 3/2023 | | |

OTHER PUBLICATIONS

International Search Report and Written Opinion in International Appln. No. PCT/US2022/041992, mailed on Dec. 19, 2022, 16 pages.
International Preliminary Report on Patentability in International Appln. No. PCT/US2022/041992, mailed on Mar. 14, 2024, 10 pages.

* cited by examiner

*Primary Examiner* — Celeste A Roney
(74) *Attorney, Agent, or Firm* — Fish & Richardson P.C.

(57) ABSTRACT

Methods and systems are provided to determine efficacy of a medical treatment by monitoring biomarkers of a patient undergoing the medical treatment. The monitoring is performed by sensors that are attached to the patient while the patient is performing his/her normal life. For example, the sensors can be worn similar to a watch, a headband, a belt, etc.

20 Claims, 8 Drawing Sheets

*300*

Receive biomarker baseline for a patient — *302*

Receive raw signal subsequent to starting a medical treatment — *304*

Obtain a biomarker associated with the raw signal — *306*

Compare the biomarker to the biomarker baseline — *308*

Determine efficacy of the treatment based on the changes in the biomarker — *310*

Modulate the treatment based on the determined efficacy — *312*

*340*

Receive biomarker baseline for a subject having a medical condition  *342*

Receive raw signal subsequent to starting a medical treatment  *344*

Obtain a biomarker associated with the raw signal  *346*

Determine the progress of the medical condition by comparing the biomarker to the biomarker baseline  *348*

EVALUATING DRUG EFFICACY BY USING WEARABLE SENSORS

CROSS REFERENCE TO RELATED APPLICATIONS

This application claims priority to U.S. Provisional Application No. 63/239,213, filed on Aug. 31, 2021, U.S. Provisional Application No. 63/342,815, filed on May 17, 2022, and EP Application No. 21315235.8, filed on Nov. 5, 2021, the entire contents of which are incorporated herein by reference.

BACKGROUND

Achondroplasia is a rare disease and the dominant form of dwarfism. It is due to a mutation of the fibroblast growth factor 3 (FbGF3) gene. Achondroplasia causes severe complications in the skull (foramen magnum stenosis and midface hypoplasia) leading to sleep apnea, in addition to vertebral and long bone formation complications altering the gait (*varus* or vargus gait) and muscle fatigue decreasing patient mobility and physical activity. These complications decrease patient quality of life (QOL) in terms of poor sleep quality and reduced mobility.

Currently, the severity of achondroplasia and therapy efficacy are assessed in clinic at intermittent times, requiring the patient to commute to a hospital/healthcare facility each time. Brain MRI is used to monitor foramen magnum growth, and polysomnography is used to assess sleep-apnea during in clinic overnight stay. Gait and physical activity are also assessed in clinic by asking the patient to perform repetitive tiring tasks while a physician evaluate the performance, albeit rather subjectively.

SUMMARY

Implementations of the present disclosure include methods and systems for monitoring biomarkers (i.e., biological characteristics) of a patient by wearable sensors attached to the patient, and evaluating those biomarkers by applying signal processing and AI (deep and machine learning) algorithms to the wearable data to diagnose a disorder or to determine a change in the patient's medical condition. The change can be the result of a medical treatment performed on the patient. Accordingly, the implementations provide a technique to determine efficacy of a medical treatment on improving a disorder in a patient by evaluating the changes in the patient's biomarkers as a result of the medical treatment.

As an example, the implementations can be applied to diagnose achondroplasia and/or to evaluate any changes in biomarkers of patients who suffer from achondroplasia, and to determine efficacy of a medical treatment in improving patient's condition by tracking these biomarkers. Example biomarkers include the sleep pattern, the gait posture, and the physical activity of the patients.

The present disclosure teaches using biomarkers for continuous monitoring of sleep apnea, gait, and physical activities in the achondroplasia patients. The continuous monitoring can be performed while the patient is at home, at work, on vacation, etc. The patient wears one or more wearable devices configured to monitor biological biomarkers, e.g., oxygen saturation, step counts, etc. of the patient. The wearable devices produce signals that contain the biological biomarker data. The wearable devices transmit the signals to a backend system. The backend system analyzes the signals to compute digital biomarkers, e.g., apnea hypopnea index, gait measurements, physical activity measures, etc., from the signals.

The digital biomarkers can be used for a variety of purposes. For example, the digital biomarkers can be used to determine the quality of life of the patient, e.g., compared to a healthy person sharing similar biological characteristics, e.g., age, race, sex, etc.

The changes in digital biomarkers over time can be used for a variety of purposes. For example, a change in the digital biomarkers can be used to determine the progress of a medical condition of the patient, the efficacy of a particular medical treatment in improving the medical condition of the patient, the efficacy of the medical treatment in improving the medical condition of a group of patients taking the treatment as compared to another group of patients not taking the treatment.

Some implementations include a computer-implemented method executable by a computing system. The method includes: receiving one or more biomarker baselines for a patient, the biomarker baselines representing biological characteristics of the patient before going through a medical treatment; receiving, from a client device, one or more signals representing respective biomarkers of the patient measured over a period of time subsequent to starting the medical treatment, wherein the signals are generated by one or more wearable sensors that are worn by the patient to measure the biomarkers over the period of time; analyzing the signals to obtain the respective biomarkers; determining efficacy of the medical treatment by comparing each of the obtained biomarkers with one or more respective biomarker baselines to determine respective changes in the biomarkers, and by comparing the respective changes with respective threshold values to determine the efficacy of the medical treatment on the patient; and storing or presenting the determined efficacy for the medical treatment. The determined efficacy can be used for modulating the medical treatment.

The biomarkers can include two or more of sleep apnea, gait, or physical activity. When a biomarker is sleep apnea, the method can include calculating an apnea hypopnea index based on the received signals. Determining the efficacy of the medical treatment can comprise determining a change in the apnea hypopnea index, and marking the medical treatment as effective in response to determining a decrease in the apnea hypopnea index for more than a particular threshold value. When the biomarkers include gait or physical activity assessments, the signals can be based on measurements of one or more of gait speed, step length, step duration, or physical activity measure of the patient.

At least one signal can include data measured continuously over hours each day during the period of time.

The medical treatment can be a treatment for pediatric achondroplasia patients.

The medical treatment can include consuming a drug. The method can further include: receiving respective measurement signals from multiple client devices respectively worn by multiple patients; determining respective biomarkers for each of the multiple patients based on the respective measurement signals; determining one or more dosages of the drug that causes the desired changes (e.g., the most changes) in the respective biomarkers in at least some of (e.g., each of) the multiple patients; determining, from among the one or more dosages, a particular dosage that causes the desired changes (e.g., the most changes) in biomarkers on most of patients in the multiple patients; and storing or reporting the particular dosage as a recommended dosage for the drug.

Analyzing the signals to obtain the respective biomarkers can include: filtering each of the received signals to cleanse the signal for a particular range of frequencies; and applying AI models on the cleansed signal to estimate the measured biomarkers based on patterns detected in the signal over the period of time.

In some implementations, the client device is remote from the computing system, and data of the signals are received from the client device through one or more wireless communication links. In some implementations, the client device includes at least one sensor in the one or more wearable sensors.

Some implementations cover a computer-implemented method for measuring the quality of life of patients (e.g., pediatric patients) having achondroplasia. The method can be performed by one or more processors and including: receiving first signals from a first device over a first plurality of time periods, each first time period in the first plurality of time periods being indicative of an awake time period of the patient during which the first device is worn substantially continuously by the patient; determining a mobility measurement of the patient based on the first signals; receiving second signals from a second device over a second plurality of time periods, each second time period in the second plurality of time periods being indicative of a sleeping time period of the patient during which the second device is worn substantially continuously by the patient; determining a severity of sleep apnea experienced by the patient based on the second signals; and determining an indicator of the patient's quality of life based on the mobility (e.g., gait measurements and/or physical activity) and sleep quality (e.g., the severity of sleep apnea).

The method can further include determining an improvement in the quality of life by determining at least one of an improvement in the mobility measurement or a reduction in the sleep apnea.

An improvement in the quality of life can be determined by determining a reduction in the severity of sleep apnea. Determining the severity of the sleep apnea can include: calculating an apnea hypopnea index (AHI) from data extracted from the second signals; and comparing the AHI to one or more predefined AHI thresholds. The AHI can be calculated per hour of sleep for each of the second plurality of time periods.

The second signals can include information on oxygen saturation in blood of the patient, plethysmogram signals, or both.

The first signals can include information of tri-axial acceleration of the patient when the first device is worn by the patient over the first plurality of time periods, wherein the mobility measurement (e.g., an activity level) of the patient is determined based on the information of the tri-axial acceleration. The method can include obtaining data representing one or more biomarkers of the patient from the first signals, wherein the mobility measurement of the patient is determined based on the one or more biomarkers.

The mobility measurement can include measurement of one or more gait parameters such as gait speed, step or stride duration, step or stride length, or step counts of the patient. Changes in these gait measures can show an improvement in mobility. An improvement in mobility is an indicative of an improvement in the quality of life of the patient. Accordingly, an improvement in the quality of life of the patient can be determined by determining at least one of an increased gait speed (e.g., waling speed), an increased (i.e., a longer) step/stride length, and/or a decreased (i.e., a shorter) step/stride duration.

The present disclosure provides a computer-implemented method of implementing a clinical trial on a plurality of participants. The method includes: receiving a first set of signals from a first set of wearable devices, each of the first set of wearable devices being worn substantially continuously by a respective participant in the plurality of participants; determining from the first set of signals a respective severity of sleep apnea (or a respective sleep quality, in general) experienced by each of the plurality of participants; receiving a second set of signals from a second set of wearable devices, each of the second set of wearable devices being worn substantially continuously by a respective participant in the plurality of participants; determining from the second set of signals a measure of mobility for each of the respective participants; identifying an experimental group of participants from the plurality of participants, each participant in the experimental group having been given a particular drug in the clinical trial; and determining a result of the clinical trial based, at least in part, on comparing (i) the severities of sleep apnea and the measures of mobility of the participants in the experimental group, to (ii) the severities of sleep apnea and the measures of mobility of one or more participants in the plurality of participants that are not in the experimental group. A wearable device is worn substantially continuously over time period if, for example, the ratio of time worn during that time period versus time not worn during that time period is greater than a predetermined value.

The method can further include identifying a control group of participants in the plurality of participants, each participant in the control group having been excluded from being given the particular drug for the clinical trial. In other words, the patients in the control group are not given the particular drug.

Alternatively or in addition, the method can further include assigning (e.g., randomly) the control group of participants from the plurality of participants; none of the participants in the control group is given the experimental drug.

The measure of mobility for a participant can be determined based on the gait, the physical activity, or both, of the participant.

The method can further include measuring sleep quality and mobility of participants of both experimental and control group. Determining the result of the clinical trial can include comparing sleep quality and mobility of these two groups. The clinical trial can be determined as effective when (i) sleep quality is better (e.g., lower AHI) in the experimental group as compared to the control group (ii) mobility has improved (e.g., increased gait speed) in experiment group as compared to the control group, or (iii) both (i) and (ii).

For example, the method can include: calculating a first apnea severity statistic for the participants in the experimental group, and a second apnea severity statistic for the participants that are not in the experimental group (e.g., are in the control group); and calculating a first mobility measure statistic for the participants in the experimental group, and a second mobility statistic for the participants that are not in the experimental group. Determining the result of the clinical trial can include comparing the first apnea severity statistic to the second apnea severity statistic, and comparing the first mobility measure statistic to the second mobility measure statistic. In an example, the first apnea severity statistic is calculated as the average of the severities of sleep apnea for the participants in the experimental group, the second apnea severity statistic is calculated as the average of the severities of sleep apnea for the participants that are not in the experimental group, the first mobility measure statistic is calculated as the average of the measure of mobility for the participants in the experimental group, and the second mobility measure statistic is calculated as the average of the measure of mobility for the participants that are not in the experimental group.

The clinical trial can be determined as effective when (i) the first apnea severity statistic differs from the second apnea severity statistic for more than a specified apnea threshold value, (ii) the first mobility measure statistic differs from the second mobility measure statistic for more than a specified mobility threshold value, or (iii) both (i) and (ii). For example, the clinical trial can be determined as effective when (i) the average of the severities of sleep apnea for the participants in the experimental group is less than the average of the severities of sleep apnea for the participants that are not in the experimental group for more than the specific apnea threshold value, (ii) the average of the measure of mobility for the participants in the experimental group is improved relative to (e.g., is greater than) the average of the measure of mobility for the participants that are not in the experimental group for more than the specified mobility threshold value, or (iii) both (i) and (ii).

The present disclosure discloses a computer-implemented method of monitoring progress of a medical condition on a live subject having the medical condition. The method includes: receiving one or more biomarker baselines for the live subject, the baselines representing biological characteristics of the subject measured before (e.g., right before) a first time point; receiving, by the computing system and from a client device, one or more signals representing respective biomarkers of the live subject measured over a period of time subsequent to the first time point, wherein the signals are generated by one or more wearable sensors that are worn by the subject to measure the biomarkers over the period of time; analyzing the signals to obtain the respective biomarkers; and determining a progress of the medical condition on the live subject by comparing the obtained biomarkers to respective biomarker baselines. The medical condition can be achondroplasia. The biomarkers, including the biomarker baselines, can be received continuously over a period of time as part of the signals received from the wearable sensors. The sensors can send out the biomarker information by modulating them into the signals.

The present disclosure also provides one or more non-transitory computer-readable storage medium coupled to one or more processors and having instructions stored thereon which, when executed by the one or more processors, cause the one or more processors to perform operations in accordance with implementations of the methods provided herein.

Methods and systems in accordance with the present disclosure may include any combination of the aspects and features described herein. That is, methods and systems in accordance with the present disclosure are not limited to the combinations of aspects and features specifically described herein, but also include any combination of the aspects and features provided.

Among other advantages, implementations can provide one or more of the following benefits. The implementations provide an objective evaluation of a patient's mobility and sleep quality, and as a result, can deliver a more reliable determination of the efficacy of a medical treatment on the patient's disorder. Conventionally, a clinician reviews the patient's biomarkers to determine potential disorders that the patient has. For example, a clinician observes the gait posture of a patient in an in-clinic visit to diagnose achondroplasia disorder or to determine the severity of the disorder of the patient. Such diagnosis and determination is highly subjective. As a result, one clinician may identify the disorder on a particular patient as severe and prescribe a high dosage of a medicament, while another clinician may identify the same disorder on the same patient as mild and prescribe a low dosage of the medicament or other treatment methods. The implementations of the present disclosure reduce subjectivity in monitoring and diagnosis by objectively monitoring the patient's biomarkers through sensors attached to the patient, and by using AI methods to objectively evaluate the patient's mobility and sleep measures. The implementations can also provide an objective evaluation of the efficacy of a particular medical treatment on the disorder by objectively monitoring and evaluating biomarkers of the consumers of the particular treatment before and after receiving the treatment.

Further, the implementations use sensors that are capable of monitoring the patient's biomarkers over a period of time rather than through an in-clinic spot-check. The continuous monitoring of the sensors provides a more reliable result because the results are based on a continuous monitoring of the patient over a period of time, e.g., hours, days, weeks, months, rather than based on an instantaneous observation through a limitedly timed imaging or clinician observation.

The presented implementations are capable of diagnosing a disorder and determining changes in the patient's biomarkers through a monitoring system that causes little to no interruption in the patient's daily life. While in the in-clinic procedures the patient has to interrupt their daily life to visit the clinic, and often has to be assessed by bulky instruments such as MRI, the sensors in the present implementations monitor the patient's biomarkers without requiring the patient to deviate from their daily life. Further, since the patient is being monitored while living their normal life, e.g., while being at home, the patient does not have to go through the burden of visiting a clinic or hospital, e.g., on a regular basis, to be monitored. This also reduces the healthcare costs to the patient and to the society.

The presented methods also provide a more reliable result because the results are based on a continuous monitoring of the patient over a period of time, e.g., hours, days, weeks, months, rather than based on an instantaneous observation through a limitedly timed radiation (e.g., MRI) or clinician assessments. The implementations provide a more realistic quality of life (QOL) assessment of the patient by monitoring the patient in his daily life environment and not in a controlled clinical environment.

The details of one or more implementations of the present disclosure are set forth in the accompanying drawings and the description below. Other features and advantages of the present disclosure will be apparent from the description and drawings, and from the claims.

DETAILED DESCRIPTION

Figure 1:
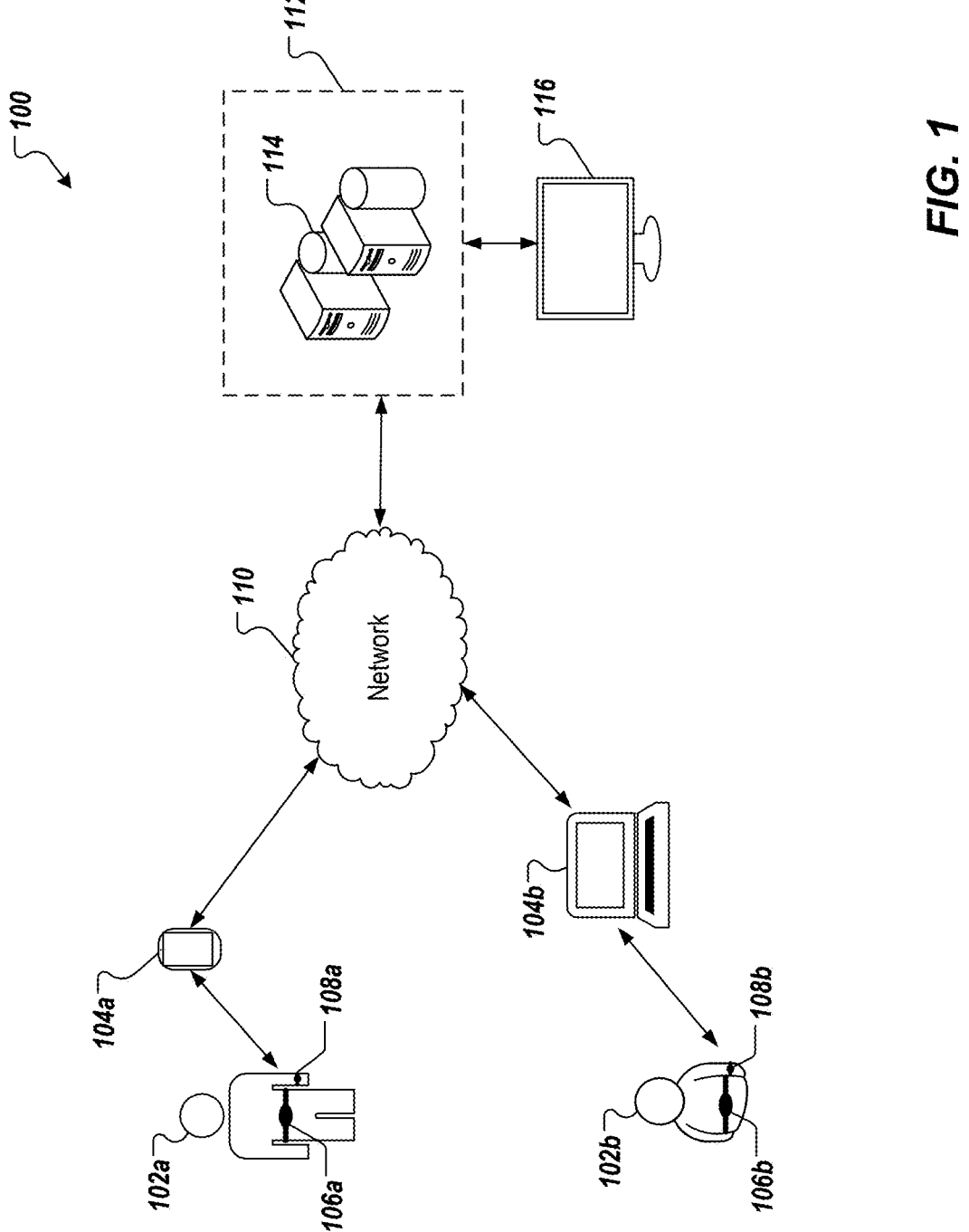
FIG. 1 depicts an example environment that can be used to execute implementations of the present disclosure.

Implementations of the present disclosure provide techniques for determining efficacy of medical treatments by monitoring biomarkers of the patients who have received the medical treatments. The monitoring is through sensors that can be worn by the patients. The sensors are intended to have little to no impact on the daily lives of the patients, and rather provide a comfortable facilitation to measure the biomarkers as compared to the conventional in-clinic assessments.

The implementations can be used to study medical treatments on a variety of disorders or diseases. For example, the implementations can be used to study effectiveness of a particular drug on a particular disorder by monitoring biomarkers of one or more patients that are taking or have recently taken the drug. The implementations analyze the changes in the patient's biomarkers to evaluate the effectiveness of the drug on the particular disorder. Such evaluation also can be used to determine an effective dosage of the drug that would provide a considerable improvement in a patient's or in a class of patients' symptoms or biomarkers without causing harsh side effects on them. The evaluation can also be used in facilitating or accelerating evaluation of drugs for getting approval from particular standards or administrations such as United States Food and Drug Administration (FDA).

The drug efficacy can be determined for individual patients, for a general public who suffers from the disease or disorder, or for both individuals and the general public. In other words, the techniques presented here can be used to personalize a medical treatment per individual patients who suffer from a disease or disorder, or can be used for determining the effectiveness of the medical treatment on the disease or disorder in general. When personalizing the medical treatment, an improvement of the individual patient's biomarkers over time can be studied. When studying the efficacy of the medical treatment in general, the improvement of biomarkers of a group of experimental patients who take the treatment over a time period can be compared to the changes in biomarkers in a group of patients who do not take the treatment over that time period. (Further, such group comparisons can also be taken into account when personalizing medical treatment for an individual.)

The present disclosure discusses monitoring sleep, gait, and physical activities as example biomarkers of a patient suffering from achondroplasia disorder. As discussed below, these biomarkers are analyzed to determine a medical improvement of the patient that could be correlated to the underlying medical treatment. These example biomarkers are particularly determinative in diagnosis of achondroplasia. While achondroplasia is an example disorder used in this disclosure to explain the implementations, a skilled person in the art would recognize that similar concepts are applicable to other disorders or diseases, for example, to determine the effectiveness of a medical treatment on those disorders or diseases.

In an embodiment, sleep apnea in a patient can be detected by using a wearable pulse oximeter worn by the patient. Apnea or hypopnea events during a patient's sleep time can be detected by applying signal processing and/or AI algorithms including deep learning or machine learning algorithms, on the oxygen saturation (SpO2) in the patient's blood, and on the plethysmogram signals of the pulse oximeter. The processing of the oxygen saturation and the plethysmogram signals can occur locally, e.g., in the oximeter device, on a mobile device, e.g., on the patient's smart phone, or on a remote device, e.g., a doctor's computer, after transferring the signal's data out of the wearable oximeter device data, e.g., to the remote device.

The techniques presented in this disclosure allow computation of the Apnea Hypopnea Index (AHI), the (average) number of apnea and hypopnea events more frequently and continuously than conventional clinical methods. For example, the computation can be performed every hour of sleep.

The AHI can be used as the digital measure (or digital endpoint) in assessing the disease severity in a patient. The AHI can be used in assessing the efficacy of a medical treatment (e.g. drug compound) on sleep apnea and on patients' quality of life (QOL) in terms of sleep quality. In an example, the AHI categorizes sleep apnea into none/minimal (AHI<5), mild (5≤AHI<15), moderate (15≤AHI<30) and severe (AHI>30). A medical treatment can be identified as showing positive effects on sleep-apnea of a particular patient, if the particular patient taking the treatment, exhibits a drop in AHI from the patient's AHI baseline. The baseline represents biological characteristics of the particular patient before going through the treatment.

The present disclosure also provides techniques for monitoring and evaluating a patient's mobility including gait and physical activity, by using a wearable actigraphy. A wearable actigraphy is a device that measures tri-axial acceleration of a patient when the device is worn on the patient's body. Actigraphy signals received from the wearable actigraphy device can be processed by signal processing and/or AI algorithms, to compute gait measures and physical activity measures. Gait can be measured, for example, based on gait speed, step or stride duration, step or stride length, step count, etc. Physical activity measure can be determined as the patient's amount of activity over a time period, for example, based on acceleration magnitude of the patient's movements.

The processing of the actigraphy signals can occur locally, e.g., on the actigraphy device, on a mobile device, e.g., on the patient's smart phone, or remotely, e.g., on a doctor's computer after transferring the actigraphy signal data out of the wearable device data, e.g., to the doctor's computer.

The gait and physical activity measurements can be used as digital endpoints to assess the disease severity in a patient. The gait and physical activity measurements can be used to assess the efficacy of a medical treatment in improving patients' QOL in terms of gait and physical activity. In an example, a medical treatment can be considered as showing positive effects on a particular patient if the particular patient exhibits an increase from a baseline in at least one of the particular patient's gait velocity, step or stride length, or step count or physical activity measure over a particular time period, e.g., daily, or exhibits a decrease in the patient's step or stride duration. In some implementations, the increase has to be a consistent increase over a specified period of time, e.g., a month, to determine that the treatment is showing positive effects on the particular patient.

In some implementations, an improvement in the patient's mobility measurements (e.g., in gait and/or in physical activity) indicates that the medical treatment had positive effects on the patient. The improvement in mobility can be determined from an improvement in patient's ability to move more freely and more easily as compared to before taking the medical treatment. The improvement can be determined from an improvement in the patient's abilities to move, for example, an increase in the patient's step length or a decrease in the duration of the step, an increase in the speed of the gait, e.g., walking speed, an increase in the patient's physical activity measures, etc.

FIG. 1 depicts an example environment 100 that can be used to execute implementations of the present disclosure. FIG. 1 shows two patients 102a and 102b. One or more sensors are attached to each of the patients. A sensor can be in form of a belt, a watch, a headband, a chest band, an ankle monitor, or any other wearable devices that can be attached to or worn by a patient. Patient 102a is wearing sensors 106a and 108a, and patient 102b is wearing sensors 106b and 108b.

Each of the sensors can operate independently from the other sensors attached to a patient. Each sensor can communicate with a client device that correspond to the respective patient. In FIG. 1, sensors 106a, 108a communicate with client device 104a of patient 102a, and sensors 106b, 108b communicate with client device 104b of patient 102b.

Each sensor monitors one or more corresponding biomarkers. For example, sensors 108a, 108b can be worn in form of a watch and monitor heart rate, blood oxygen, temperature, etc., and sensors 106a, 106b can be in worn in form of a belt to monitor gait and physical activities of the respective patients.

The data obtained by the sensors are ultimately sent as a raw signal (i.e., raw data) to a backend server 112 for evaluation and analysis. A raw signal includes data related to a particular biomarker of the patient. The backend server 112 analyzes the raw signal to provide the biomarker represented by the raw data.

In the implementation shown in FIG. 1, each sensor sends raw data to a respective computing device 104a, 104b, and the computing devices forward the raw data to the backend server 112. In some implementations, a sensor can communicate directly with the backend server, e.g., through a wireless communication such as satellite communication, Internet, wireless local area network (WLAN), etc.

In FIG. 1, each of the sensors 106a, 106b, 108a, 108b can communicate with a respective client device 104a, 104b over a respective wireless communication link. This wireless communication link can be of a low-power communication protocol, e.g., Bluetooth. Alternatively or in addition, the sensors can transfer data to the client devices through a wired communication. For example, a sensor may be part of a device that is capable of saving the data locally, and transferring the data when connected to the client device through a wired connection.

Each of client devices 104a, 104b is connected to the backend server 112, for example, through a wireless network 110. Backend server 112 includes one or more computing systems 114 capable of analyzing and evaluating raw data received from client devices 104a, 104b. The output of this analysis and evaluation would be respective biomarkers associated with the raw data.

Backend server 112 analyzes the received biomarker data by comparing each biomarker to a respective biomarker baseline to determine a change in the biomarker that can be associated to a medical treatment that the patient is taking or has recently taken. The backend server compares the biomarker changes to specific threshold values or patterns to determine the efficacy of the medical treatment.

For example, sensor 106a can measure data related to gait and physical activity of patient 102a over a specific period of time (e.g., two weeks) post taking a particular drug. The backend server 112 receives raw data to obtain the biomarkers for the measured gait and physical activity and determines whether on average the patient 102a has shown faster (as a value) or more frequent (as a pattern) movements during that specific period of time. Since physical activity and gait are biomarkers used to diagnose the severity of achondroplasia, the changes in theses biomarkers can be associated to the drug taken. For example, if the biomarker data shows a more frequent (e.g., more than twice the frequency in the baseline) or longer episodes of continuous walking (e.g., fifty percent longer than similar episodes in the baseline) of patient 102a as compared to the baseline biomarker, the backend server 112 can determine the medical treatment as effective.

A biomarker baseline is a pretreatment value or pattern of a biomarker that is measured before administration of the medical treatment on the patient, e.g., before the patient takes a particular drug. The value can be calculated as a mean, a median, etc. of the biomarker over a period of time; for example, an average number of apnea episodes per hours of sleep before the patient goes under a particular medical treatment. The pattern can be, for example, the pattern of maximum/minimum values, steadiness periods, sharp changes, etc. of the biomarker over a period of time; for example, walking pattern of the patient per day over a week prior to going under a particular medical treatment. The biomarker baseline can extracted from the signals received continuously from the sensors over a period of time before the patient takes the particular drug.

Backend server 112 can retrieve the biomarker baseline for a particular patient from a storage device. The backend server 112 can retrieve a biomarker baseline that is saved as a general baseline for patients that have biological characteristics (e.g., age, gender, medical history) similar to a particular patient that is being monitored, e.g., patient 102a.

Alternatively, backend server 112 can obtain or calculate a personalized biomarker baseline for the particular patient, e.g., patient 102a (who is being monitored) based on the particular patient's biomarker data measured and calculated before administration of the medical treatment. For example, patient 102a may be asked to wear sensor 106a for a specific period of time, e.g., two weeks, prior to starting of a medical treatment. Backend server 112 receives the pre-treatment data from sensor 106a and uses this data to determine a value or pattern in the monitored biomarker and to assign that values or patterns as the baseline of the monitored biomarker for the particular patient 102a.

Compared to conventional diagnosis or monitoring methods, sensors 106a, 108a are intended to disturb patient 102a's daily life as little as possible. Sensors 106a, 108a can be worn for continuous hours throughout the monitoring period of time.

For example, sensor 108a can be in form of a watch wearable around the patient's wrist to monitor physiological parameters of the patient. For example, sensor 108a can be worn during the sleep time of patient 102 to monitor sleep pattern of the patient. Sensor 108a can include a pulse oximeter to monitor the oxygen level in the patient's blood and produce a signal that reports the oxygen level throughout the sleep time. By reviewing the data of this signal, the backend server 112 can detect when and for how long the oxygen level dropped below a predetermined threshold value, which is an indicator of a sleep apnea episode.

As another example, sensor 106a can be in form of a belt that would monitor spatial movements of patient 102a's body, and reports signals indicative of changes in the position of the body (i.e., mobility measures). Sensor 106a can include one or more accelerometers or actigraphy sensors that each measures acceleration in a particular direction, e.g., X-axis, Y-axis, and Z-axis. By reviewing these signals, backend server 112 can determine the movement acceleration, frequency, orientation, etc. of patient 102a over the period of time that the sensor is worn and active.

To analyze the raw data, backend server 112 applies signal processing and AI algorithms on raw signals representing the raw data. The algorithms include machine learning and neural network models that are particular to the biomarkers represented by the raw data.

Figure 2A:
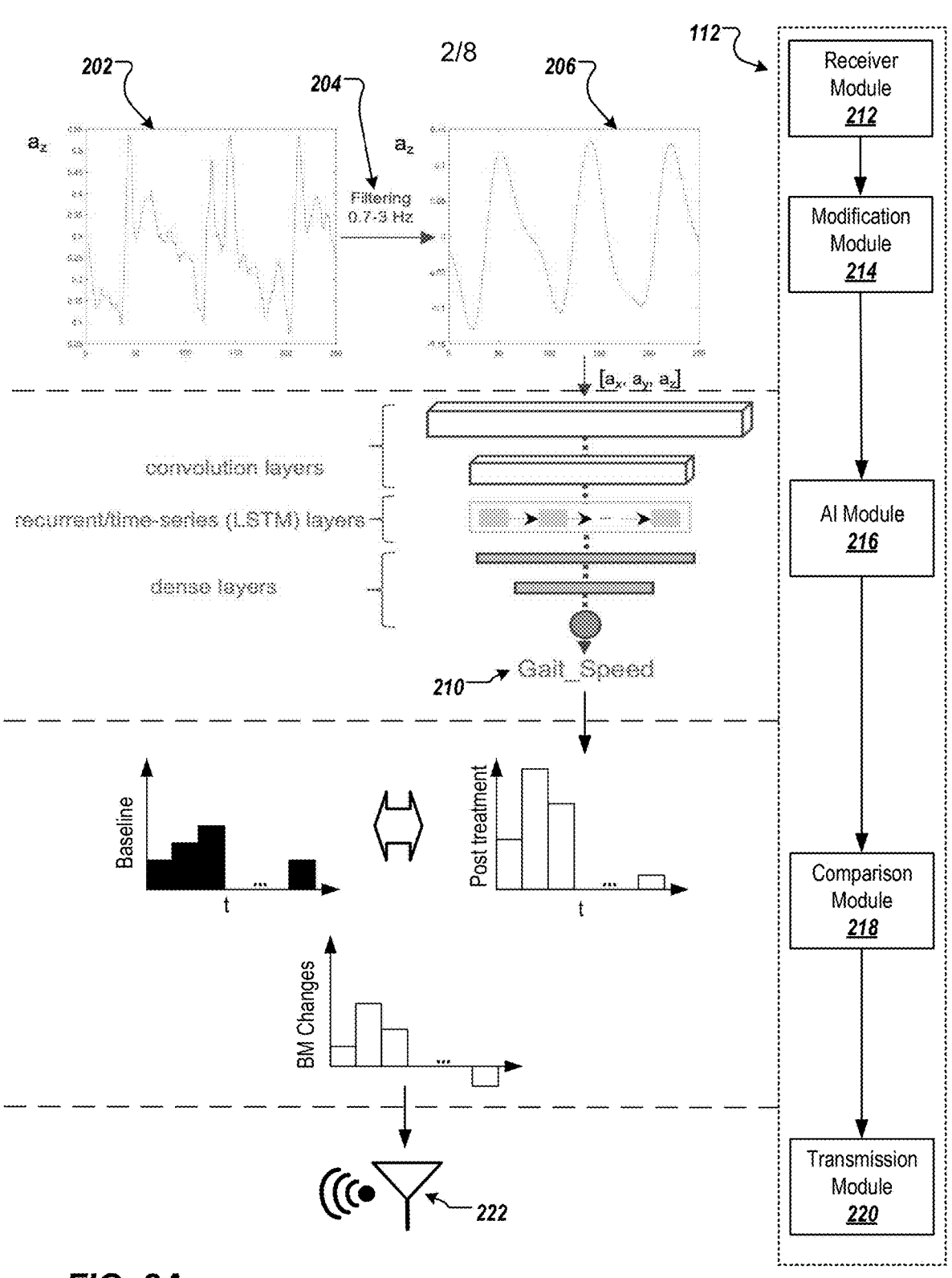
FIG. 2A depicts example components of a system capable of analyzing raw signals received from wearable devices attached to a patient and determining efficacy of a medical treatment.

FIG. 2A illustrates example components of background server 112 as a system that is capable of analyzing raw signals and determining efficacy of a medical treatment on a particular patient, e.g., patient 102a in FIG. 1. The system is configured to run a deep learning model on signals received from a device to determine the gait speed. The example components includes receiver module 212, modification module 214, AI module 216, comparison module 218, and transmission module 220.

In this example, background server 112 receives raw signal 202 through the receiver module 212. The receiving module can include an antenna and a communication circuitry for receiving the raw signals. The raw signal 202 is a measurement of patient 102a's gait over a period of time. Receiver module 212 forwards the raw signal 202 to modification module 214.

Modification module 214 processes the raw signal 202, for example, to cleanse the signal from noises. For example, modification module 214 can apply one or more band pass filters on the raw signal 202 to limit the data to particular frequencies. The particular frequencies can be determined based on parameters of the raw signal (i.e., what biomarker is being monitored, e.g., acceleration, movement, or orientation), biological class or parameters (e.g., age, medical history, gender, etc.) of the patient, the disorder that is being treated, or any other parameter that defines a classification of the biomarker associated with the raw signal, the patient's biology, or the disorder. Modification module 214 sends the cleansed signal 206 to AI module 216.

AI module 216 applies an AI algorithm on the cleansed data to evaluate the raw signal and obtain the biomarker represented by the raw signal. In the depicted example, the input of the AI module 216 is the cleansed signal 206, which can also be presented as data sets of three-dimensional special position $[a_x, a_y, a_z]$ of patient 102's body representing the patient's gait over time. The output of AI module 216 is a value/pattern 210 calculated as the biomarker for a particular segment of the cleansed signal 206. The particular segment can be a segment of the time period over which the patient's gait has been measured. In the depicted example, the calculated value/pattern 210 is a gait speed, which can be a value representing the gait speed over a particular segment of the time period. The AI module 216 provides the calculated value/pattern 210 to comparison module 218.

Comparison module 218 compares the values/patterns 210 for each segment, to a baseline value/pattern associated with a similar segment to determine the changes in the biomarker. For example, comparison module 218 compares gait of patient 102a measured during different hours of the day and night (e.g., midnight to 7 am, 7 am to noon, noon to 5 pm, 5 pm to 9 pm, and 9 pm to midnight), to the same hours on biomarker baseline data. The output of comparison module 218 is biomarker (BM) changes representing the differences between the calculated values/patterns 210 and the baseline biomarker.

Backend server 112 can include a transmission module 220 capable of reporting or sending the biomarker changes to a display device. For example, the backend server 112 may send the biomarker changes back to the client device 104a (see FIG. 1) for display, or may send the biomarker changes to a third-party display, e.g., display 116 (see FIG. 1). The third-party display can be associated with the patient's physician who can review the biomarker changes there and make an evaluation of the patient's improvements due to use of the medical treatment. The transmission module 220 can include an antenna 222 for wireless transmission of the data.

Alternatively, or in addition, the backend server can save the biomarker changes on a storage device. Once enough patients have been monitored, the backend server can use the stored data of the collection of the patients to determine efficacy of a medical treatment on general population (rather than on a particular patient). For example, the server may determine that on average, patients have shown a 20 percent increase in their physical activities (e.g., hours of moving at a speed greater than a threshold pace) due to the medical treatment. The backend server 112 compares the average improvement to a predefined threshold to determine whether or not the drug can be considered as effective.

Backend server 112 can perform further analysis to also recommend a medication plan, e.g., drug dosage, for treating the disorder. For example, the backend server can review drug consumption procedures such as drug dosage, frequency of drug consumption, treatment periods performed on the collection of patients, and categorize effectiveness of a drug based on those consumption procedures. In some implementations, backend server 112 recommends the drug consumption procedure that has shown the most improvements on biomarkers of the collection of patients as the general or default treatment plan for consumption of the drug.

While the methods described herein can be used to determine the efficacy of a medical treatment on the general public, a skilled person in this field would recognize that similar methods can be used to determine efficacy of the medical treatment on particular classes of the patients. For example, the patients can be classified based on one or more of their biomedical or physiological parameters such as age, gender, medical history, genes, blood type, etc., and backend system 112 may recommend a different treatment plan for each of the classes of patients.

Similarly, when evaluating biomarkers or determining efficacy of a medical treatment, the backend server 112 may use different threshold values or patterns for children than for adults. For example, while backend server 112 assesses gait as a biomarker of an adult patient in diagnosing the severity of the patient's achondroplasia, the backend server may not use the same biomarker for children under 2 years of age, who may not have started walking yet.

The implementations can also be used to personalize medication. The backend server 112 can review the biomarker data of a particular patient to determine specific physiological parameters of the particular patient, and also to monitor the changes in the particular patient's biomarkers as a result of undergoing a medical treatment. The backend server 112 can monitor effects of changes to the treatment on the particular patient's biomarkers, and as a result, can optimize the medical treatment for the particular patient. The optimization can include setting up a treatment plan such as a medicament dosage to take, the frequency of taking such medicament, combining the medicament with other drugs, etc. to improve the particular patient's biomarkers as much as possible before seeing too much undesired side effects of such treatments on the particular patient.

Figure 2B:
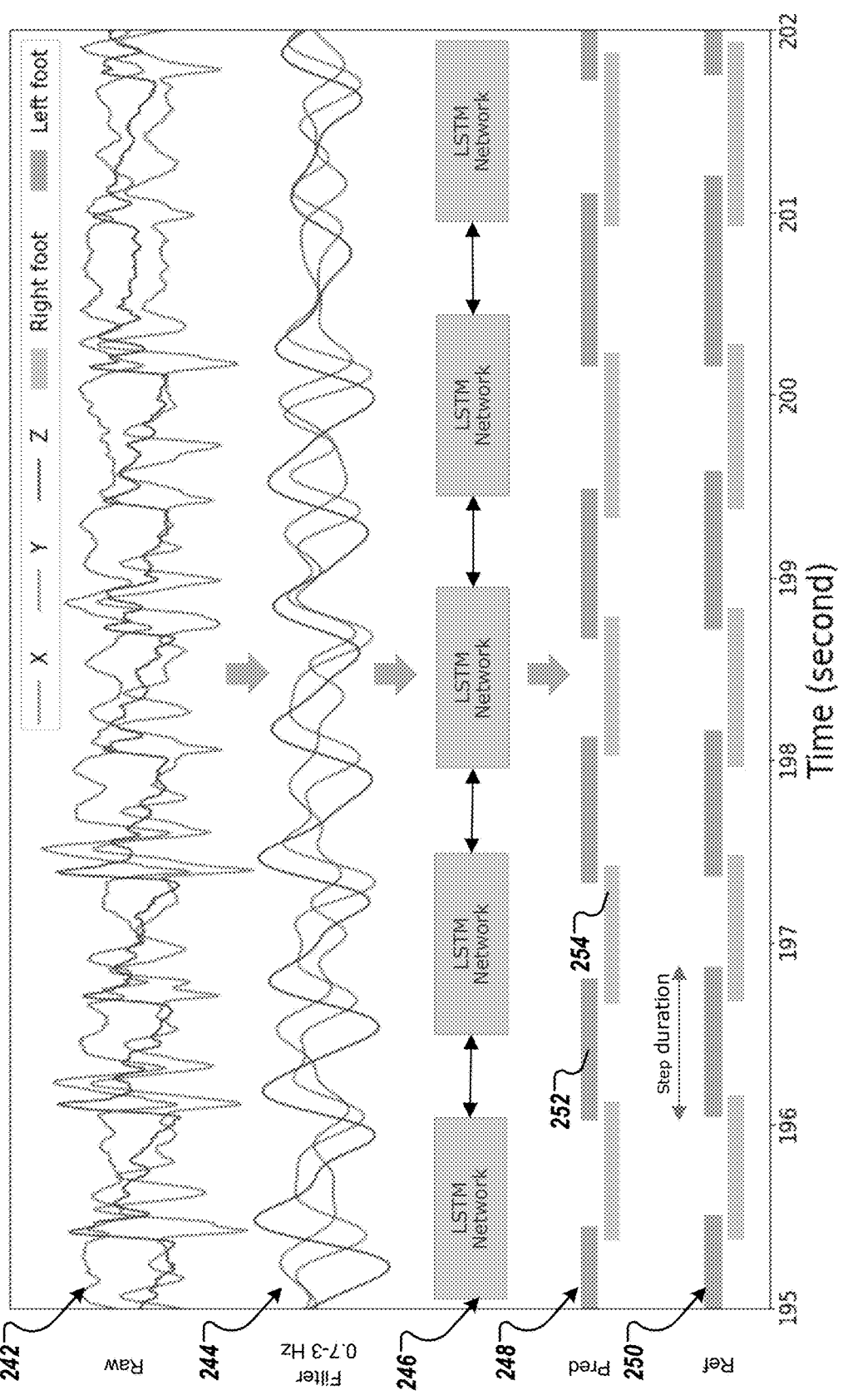
FIG. 2B illustrates an example of using an AI system to process input signals received from a device to determine step duration.

FIG. 2B illustrates an example of using an AI system to process input signals from a device (for example, a wearable device such as device 106A of FIG. 1) to determine step duration. In this example, the device provides a raw signal 242 to the system. The device can include information about the movement of the device in three orthogonal directions in three dimensional space (in this example, labeled X, Y, and Z).

The raw input signal 242 may be filtered to reduce noise and to identify signals that are more likely to be associated with the wearer of the device taking a step. For example, the filter may remove signals that are outside of a particular range. In some implementations, the filter is configured to generate a filtered signal 244 that keep the raw signals 242 that fall between the range of 0.7 to 3 Hertz.

The filtered signal can be provided to a deep learning network 246. In this example, the deep learning network 246 is based on long short-term memory (LSTM) nodes. LSTM is an artificial recurrent neural network (RNN) architecture. Unlike standard neural networks, LSTM has feedback connections. Accordingly, the system processes not only single data points but also entire sequences of data, in this case the signals indicating a change in the orthogonal directions.

The deep learning network 246 can be trained using reference data (represented for comparison purposes as ref 250). Once trained, the AI model 246 can predict 248 the left and right steps of the patient wearing the device.

Using an LSTM Network as the deep learning network 246 has particular advantages over other techniques. For example, this LSTM network is able to detect whether portion of the raw signal 242 is associated with a step with a left step 252 or a right step 254 of the individual. In some implementations, the step duration can be determined based on the duration of time that it takes from the start of the left or right step until the end of the left or right step.

In some implementations, a step duration over a time interval can be calculated based on, for example, an average of the calculated step durations, the median step duration, a range of step durations based on the 25%-75% quartile of steps, or other known method for summarizing a series of discrete similar events of a time period. In some implementations, step duration may be tracked and/or summarized separately for left steps and right steps. In other implementations, the step duration may be calculated based on a combination of left and right step information.

Figure 3A:
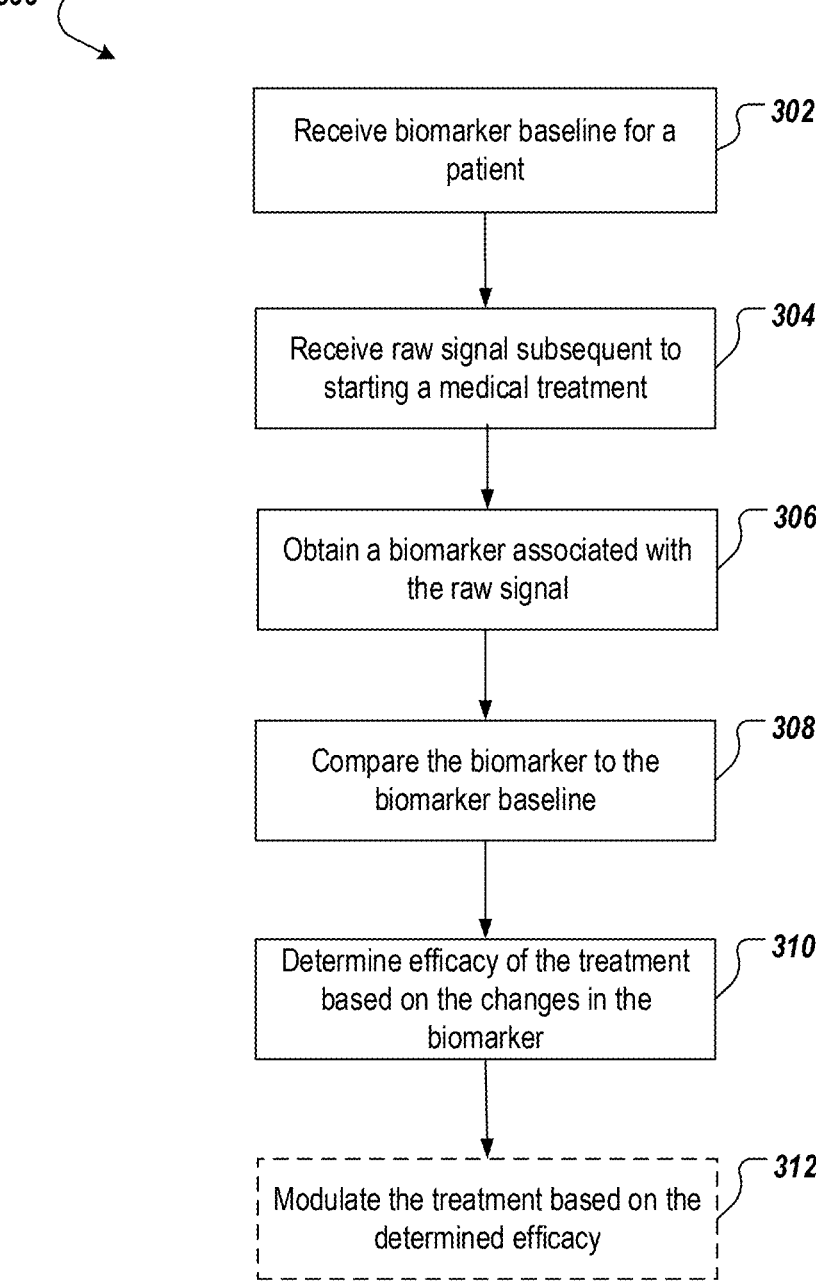
FIGS. 3A through 3D depict example processes that can be executed in accordance with implementations of the present disclosure.

FIG. 3A depicts an example process 300 that can be executed in accordance with implementations of the present disclosure to determine efficacy of a medical treatment for a particular medical disorder. Process 300 can be performed by a computing system, e.g., the backend server 112 depicted in FIG. 1.

The computing system receives one or more biomarker baselines for a patient (302). The system can obtain the biomarker baselines from a storage device, or by evaluating raw data from sensors that are attached to the patient to monitor the patient's biomarkers prior to starting a target medical treatment. Examples of such sensors are explained above, and are shown as sensors 106a, 108a in FIG. 1.

The computing system receives one or more post-treatment raw signals subsequent to starting the target medical treatment (304). One or more sensors (e.g., sensors 106a, 108a) attached to the patient monitor the biomarkers of the patient and send corresponding raw signals to the computing system, either continuously or periodically. The sensors can be wearable sensors to avoid interrupting the patient's daily life. The computing system analyzes the raw signals to obtain the corresponding biomarkers (306).

The computing system receives the raw signals over a period of time subsequent to a starting time of the medical treatment. In some implementations, the computing system starts receiving and analyzing the biomarker signals as soon as the medical treatment starts. In some implementations, the computing system receives or starts analyzing the raw signals after a transition time passes post starting the medical treatment. For example, if a drug generally starts its effectiveness after three days, the computing system may start receiving or analyzing the raw signals three or more days after the patient starts using the drug.

The computing system compares the post-treatment biomarkers calculated at 306 to the biomarker baselines received at 302 to determine any changes in the biomarkers that can be associated to the medical treatment (308). The computing system then determines the efficacy of the medical treatment based on the changes in the biomarkers (310). For example, the computing system may compare the changes to respective threshold values, and in response to determining that one or more of the changes are greater than the respective threshold values, determine that the medical treatment is effective. The medical system can also determine which ones of the biomarkers responded the most or the least to the medical treatment, or what biomarker changes can be read as side effects of using the medical treatment.

In some implementations, the computing system modulates the medical treatment based on the determined efficacy (312). For example, the computing system may suggest to a user to apply a particular change to the medical treatment to improve the effectiveness of the medical treatment on the patient. The computing system can make such suggestions in response to determining that the efficacy of the medical treatment on the patient was not as expected. The expected efficacy may be determined based on a history of efficacies of the medical treatment on other patients. The modulation can include a change the dosage of a drug, a change in the frequency of consuming a drug, adding or removing particular drugs, etc.

In some implementations, the computing system transmits the determined efficacy to another device, e.g., client device 104a. The determined efficacy can be presented on a display, e.g., display 116, can be stored in a data storage, or can be transmitted out of the backend server.

In some implementations, the computing system can determine the efficacy of the medical treatment on a class of patients. To do so, the computing system determines the biomarker for multiple patients in the class of patients, and determines one or more treatment plans (e.g., one or more dosages of a target drug) that have caused the most changes in one or more biomarkers in each of the multiple patients. From among the one or more treatment plans, the computing system then determines a particular plan (e.g., a particular dosage) that causes the most changes on most of the patients in the multiple patients. The computing system can store or report the particular plan as a recommended plan for this class of patients.

In patients with achondroplasia disorder, sleep apnea, gait, and physical activity of the patients are biomarkers that are particularly of interest. These biomarkers can indicate the severity of the disorder. The computing system can use one or multiple of these biomarkers to determine efficacy of a medical treatment.

For example, the computing system (e.g., backend server 112) can calculate an apnea hypopnea index for a patient (e.g., patient 102a in FIG. 1) by analyzing the raw signals received from the sensors that are attached to or worn by the patient (e.g., sensor 108a in FIG. 1) and monitor the patient's sleep pattern. The computing system can determine the efficacy of a medical treatment on treating or alleviating achondroplasia by determining a change in the apnea hypopnea index. The computing system can mark the medical treatment as effective in response to determining a decrease in the apnea hypopnea index, for example, where the decrease is for more than a particular threshold value, e.g., more than 20 percent decrease.

Similarly, the computing system can monitor the gait and/or physical activities of the patient to evaluate the effectiveness of a medical treatment that the patient is taking or has recently taken on his achondroplasia disorder. For example, the computing system can measure one or more of gait speed, step length, step duration, or movement acceleration of the patient (e.g., patient 102a in FIG. 1) based on the signals received from corresponding sensors worn by the patient (e.g., sensor 106a).

Process 300 can be used to determine novel pharmaceuticals for use in particular medical conditions, e.g., in treating achondroplasia. Processes similar to process 300 can be developed for pharmaceutical testing of the medical treatment. For example, drug screening, toxicity, safety, and/or pharmaceutical efficacy can be determined by monitoring the changes in biomarkers of one or more patient who have used the drug.

As discussed above, the computing system uses a respective AI model to evaluate each of the raw signals. The AI model can be a recurrent neural network. The AI model network can include one or more convolution layers. The computing system can divide a signal into segments, and apply the corresponding signal processing and AI algorithm to each segment to extract features or patterns that would define the biomarker in that segment. By doing so, the AI model applies a deep learning model on the signal as a whole. The segmentation can be done based on time, e.g., time of the day, day of the week, etc.

In some implementations, a backend server is capable of measuring the quality of life a patient, e.g., a patient having pediatric achondroplasia, based on the signals received from monitoring devices. For example, backend server 112 shown in FIG. 1 can determine the quality of life of patient 102a based on the signals that the client device 104a receives from sensors 106a and 108a. Backend server 112 can transmit the determined quality of life back to the client device 104a, or to another computing device to be presented, e.g., on display 116, to the patient or a physician associated with the patient.

Figure 3B:
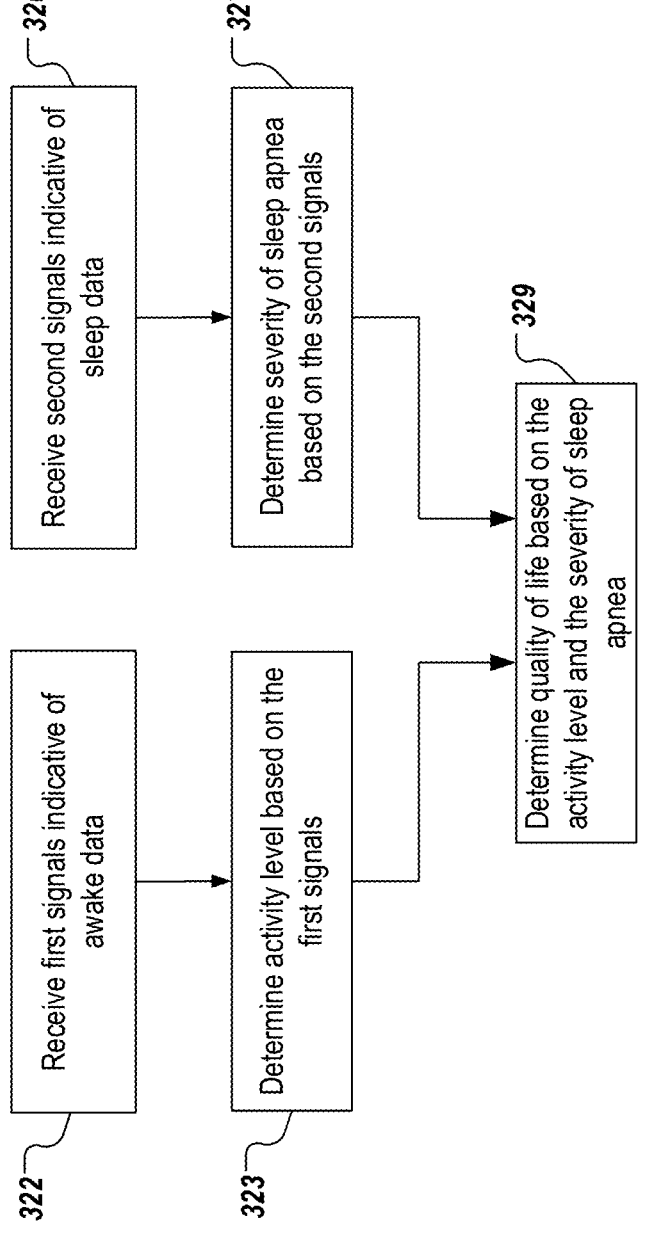

The quality of life can be determined based on the measure of mobility and the measure of the severity of sleep apnea of the patient. FIG. 3B depicts an example process 320 that can be executed in accordance with implementations of the present disclosure to determine the quality of life in a patient without requiring the patient to go to a clinic, lab, or sleep study. Process 320 can be performed by a computing system, e.g., the backend server 112 depicted in FIG. 1.

The computing system receives first signals indicative of awake data associated with a patient (322). The first signals can be received from a first wearable device including sensor 106a. Patient 102a can be provided with the first wearable device to be worn substantially continuously while patient 102a is awake. Substantially continuously as used in this disclosure means longer than a predetermined period of time before the device is taken off of the patient's body, e.g., longer than an hour, 90 minutes, etc.

The first signals can be received over a plurality of time periods, e.g., over every hour. Each time period is indicative of an awake time period during which the patient was awake and substantially continuously wore the first device.

Sensor 106a on the first device can monitor movements of patient 102a during each of the time periods and while the patient is wearing the first device. Accordingly, the patient does not need to take a break from his/her life routines, for example, to visit a physician to monitor his/her activities. Rather, sensor 106a keeps monitoring the patients activities while the patient lives his/her normal life.

The first device generates the first signals based on the movements of patient 102a that sensor 106a detects. In some implementations, the first signals include information of tri-axial acceleration of the patient when the first device is worn by the patient over the first plurality of time periods. In some implementations, the computing system receives the first signals from the first device in real time, meaning that as the patient lives his/her life, the first device monitors his/her movements and sends out first signals representing those movements to the computing system. The signal transmission may be interrupted if the patient takes the first device off his/her body, if the first device runs out of battery, or if the patient falls sleep. A respective time period may end when such interruptions happen.

Referring back to FIG. 3B, the computing system determines an activity level of the patient based on the first signals (323). The activity level can include activity-related biomarkers. In some implementations, determining the activity level includes computing gait measures for the patient. The gait measures include one or more of speed, step or stride duration, step or stride length, or step counts of the patient. In some implementations, determining the activity level includes obtaining data representing one or more biomarkers of the patient from the first signals, and determining an acceleration magnitude for the patient based on the one or more biomarkers. The activity level of the patient can be determined based on the acceleration magnitude.

The computing system can also receive second signals indicative of sleep data associated with the patient (326). The second signals can be received from a second wearable device including sensor 108a. Patient 102a can be provided with the second wearable device to be worn substantially continuously while patient 102a is awake. As noted above, substantially continuously means longer than a predetermined period of time before the device is taken off of the patient's body, e.g., longer than an hour, 90 minutes, etc.

The second signals can be received over a plurality of time periods, e.g., over every hour. Each time period is indicative of a sleeping time period during which the patient was asleep and substantially continuously wore the first device. Sensor 108a on the second device monitors the health parameters, e.g., oxygen saturation, plethysmogram signals, etc., of the patient while the patient is asleep. The second device generates the second signals based on the health parameters of patient 102a that sensor 108a detects.

Like sensor 106a and the first wearable device, sensor 108a and the second wearable device do no interrupt the patient's life routines. Sensor 108 monitors the patient while asleep, for example in his/her own bed, without requiring the patient to be present at a sleeping clinic or be attached to sophisticated machines that monitor the patient's sleep. In some implementations, the computing system receives the second signals from the second device in real time, meaning that as the patient lives his/her life, e.g., sleeps in his/her bed, the second device monitors the patient's health parameters and sends out second signals representing those health parameters to the computing system. The signal transmission may be interrupted if the patient takes the second device off his/her body, if the second device runs out of battery, or if the patient wakes up. A respective time period may end when such interruptions happen.

The computing system determines severity of sleep apnea in the patient based on the second signals (327). In some implementations, the severity of sleep apnea is determined by calculating an apnea hypopnea index (AHI) from the data extracted from the second signals. The severity can be determined based on how high the AHI is. For example, the AHI can be compared to one or more predefined AHI thresholds to determine whether the apnea is severe, medium, or mild. In some implementations, the AHI is calculated for every predetermined period of time, e.g., every hour, for each of the second plurality of time periods.

The computing system determines quality of life of the patient based on one or both the activity level and the severity of sleep apnea (329). A greater activity level can result in a greater quality of life. A greater severity of sleep apnea can result in a lower quality of life.

The example process 320 can be performed by a computing system similar to what was discussed above with respect to FIG. 2A. Indeed, the example background server 112 shown in FIG. 2A can perform one or both of the example processes 300 and 320 depicted in FIGS. 3A and 3B.

When performing process 320, the receiver module 212 is capable of receiving the first and the second signals, for example, from the first and the second wearable devices containing sensors 106a, 108a, or from an intermediary device, e.g., 104a, that is in communication with the first or the second wearable devices. The modification module 214 processes the received signals to cleanse them. The AI module 216 extracts biomarkers, e.g., gait, acceleration, oxygen level, from the signals, and determines the activity level and the severity of the sleep apnea based on the extracted biomarkers. The comparison module 218 determines the quality of life of the patient based on the activity level and the severity of the sleep apnea. The comparison module 218 may do so by comparing the activity level and the apnea severity to predetermined patterns or thresholds, and determining where the patient stands in those predetermined patterns or thresholds.

Figure 3C:
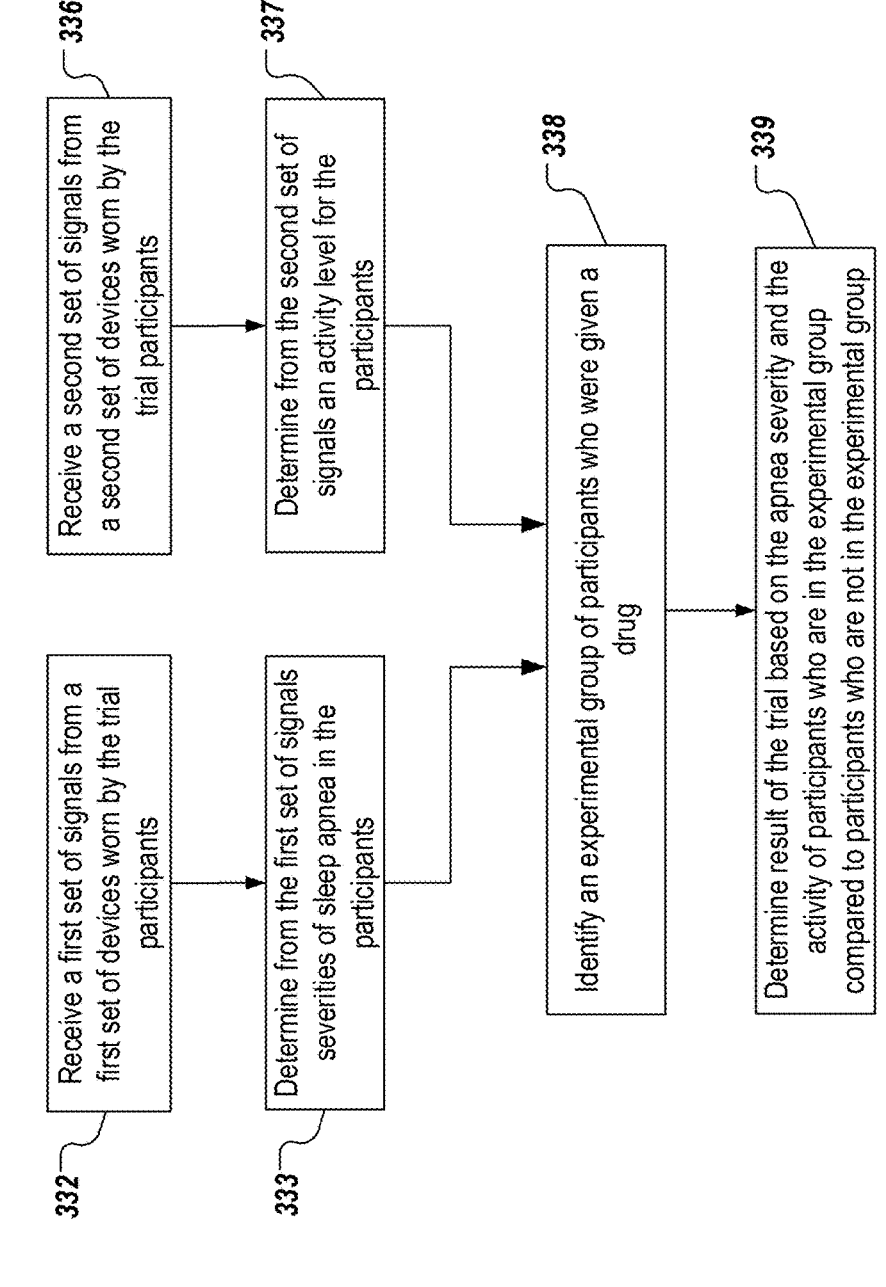

FIG. 3C depicts an example process 330 that can be executed in accordance with implementations of the present disclosure to implement a clinical trial. Process 330 can be performed by a computing system, e.g., the backend server 112 depicted in FIG. 1. The result of the clinical trial can indicate an efficacy of a particular treatment, e.g., taking a particular drug, that is being studied during the clinical trial.

The computing system receives a first set of signals from a first set of wearable devices, each of the first set of wearable devices being worn substantially continuously by a respective participant participating in the clinical trial (332). The participants can be patients or lab animals under study in the clinical trial. The first set of wearable devices can include the wearable devices that contain sensors 108a and 108b in FIG. 1. Similar to what was discussed above with respect to FIG. 3B, each of the devices in the first set of wearable devices can monitor and measure health parameters of the patient that has worn the device while the patient is asleep, and can transmit signals indicative of the measured health parameters to the computing system directly or through an intermediary device.

The computing system determines a respective severity of sleep apnea experienced by each of the participants in the trial (333). This determination can be made according to the techniques discussed elsewhere in this disclosure, e.g., as discussed for one patient in FIG. 3B.

The computing system receives a second set of signals from a second set of wearable devices, each of the second set of wearable devices being worn substantially continuously by a respective participant participating in the trial (336). For example, the second set of wearable devices can include the wearable devices that contain sensors 106a and 106b in FIG. 1. Similar to what was discussed above with respect to FIG. 3B, each of the devices in the second set of wearable devices can monitor and measure health parameters of the patient that has worn the device while the patient is awake, and can transmit signals indicative of the measured health parameters to the computing system directly or through an intermediary device.

The computing system determines a respective activity level for each of the participants in the trial (337). This determination can be made according to the techniques discussed elsewhere in this disclosure, e.g., as discussed for one patient in FIG. 3B. The activity level for patient can indicate a measure of mobility of the patient, and can indicate the gait, physical activity, etc. of the patient.

The computing system identifies (e.g., randomly) an experimental group of participants who were given a particular drug in the clinical trial (338). The computing system can make this identification randomly, or based on histories of the trial's participants, can retrieve this information from a data storage, or can prompt a user of the computing system to enter the information of participants who were given the particular drug.

The computing system determines a result of the clinical trial based on comparing the severities of sleep apnea and the activity levels determined for the participants in the experimental group compared to one or more participants in the plurality of participants that are not in the experimental group (339). In an example, the computing system determines that the trial is effective if (i) an average apnea severity in the experimental participants is less than an average apnea severity in the participants who are not in the experimental group, (ii) an average mobility in the test participants is greater than an average mobility in participants that are not in the experimental group, or (iii) both. The computing system may set a respective threshold value for each of the apnea severity and the activity level, and may compare the differences of the (average) apnea severity and the (average) activity level of the test participants and the non-test participants to the respective threshold values in order to determine the effectiveness of the trial.

In some implementations, the computing system also identifies, e.g., randomly, a control group of the participants, and compares the activity level and the sleep apnea severity of the experimental participants only to participants that are in the control group. The control group includes participants who are were not given the experimental drug for the clinical trial.

Instead of or in addition to comparing the biomarkers of the experimental and the control participants at any particular point in time, the computing system can compare the changes that occurred over a period of time in the biomarker of the participants in the experimental group to the changes that occurred in the biomarkers of the participants in the control group. Studying the changes over a period of time allows the system to analyze the effectiveness of the drug in slowing down the progress of the disease on the participants who took the drug, i.e., the experimental group, as compared to the participants who did not take the drug, i.e., the control group.

Figure 3D:
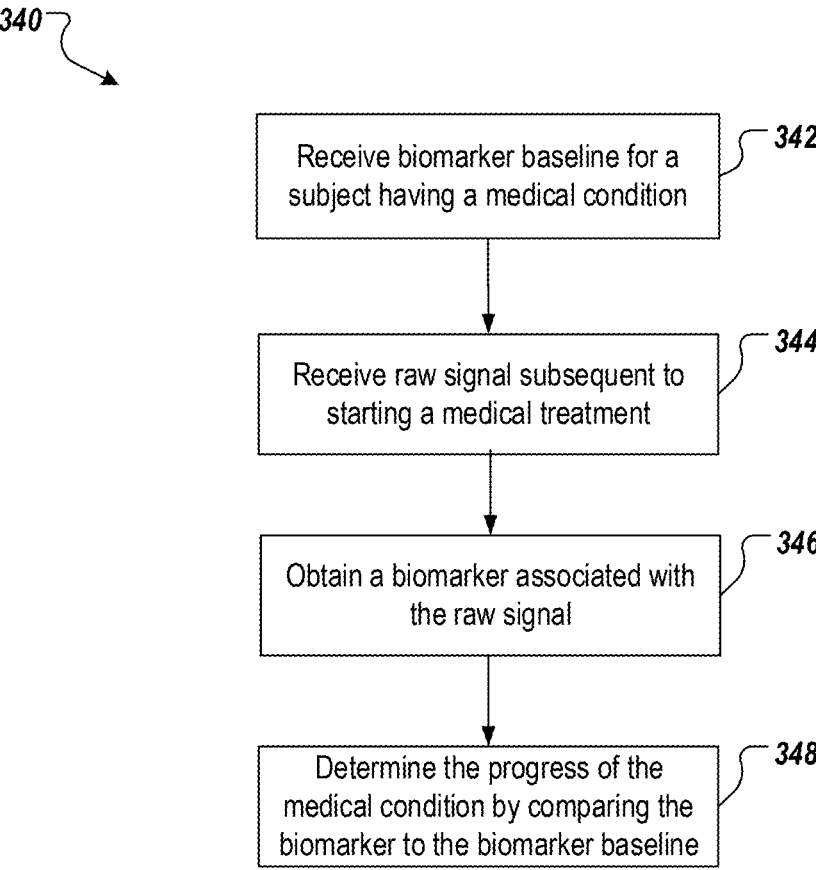

FIG. 3D depicts an example process 340 that can be executed in accordance with implementations of the present disclosure to determine the progress of a particular medical condition on a subject, e.g., a patient, a lab animal, etc. The medical condition can be achondroplasia, or any other medical disorder or disease. Process 340 can be performed by a computing system, e.g., the backend server 112 depicted in FIG. 1.

Process 340 is in part similar to process 300 depicted in FIG. 3A. Like in 302, at 342, the computing system receives one or more biomarker baselines for a subject having the medical condition. However, the biomarker baselines received at 342 represent biological characteristics of the subject measured before a particular time point.

Like in 304, at 344, the computing system receives one or more signals over a period of time, at 344. The signals are generated by one or more wearable sensors that are worn by the subject to measure the biomarkers over the period of time. However, the signals received at 344 represent respective biomarkers of the subject measured over a period of time subsequent to the particular time point. Like 306, at 346, the computing system analyzes the received signals to obtain the corresponding biomarkers.

At 348, the computing system determines the progress of the medical condition on the subject by comparing the obtained biomarkers to respective biomarker baselines. For example, if there are deterioration in sleep apnea or in activity-related biomarkers compared to the biomarker baselines, the computing system may indicate that the medical condition has gotten worse than before the particular time point.

Similar to the example process 320, processes 330 and 340 can be performed by a computing system similar to what was discussed above with respect to FIG. 2A. Indeed, the example background server 112 shown in FIG. 2A can perform one or more of the example processes 300, 320, 330, and 340 depicted in FIGS. 3A, 3B, 3C, and 3D, respectively.

Figure 4:
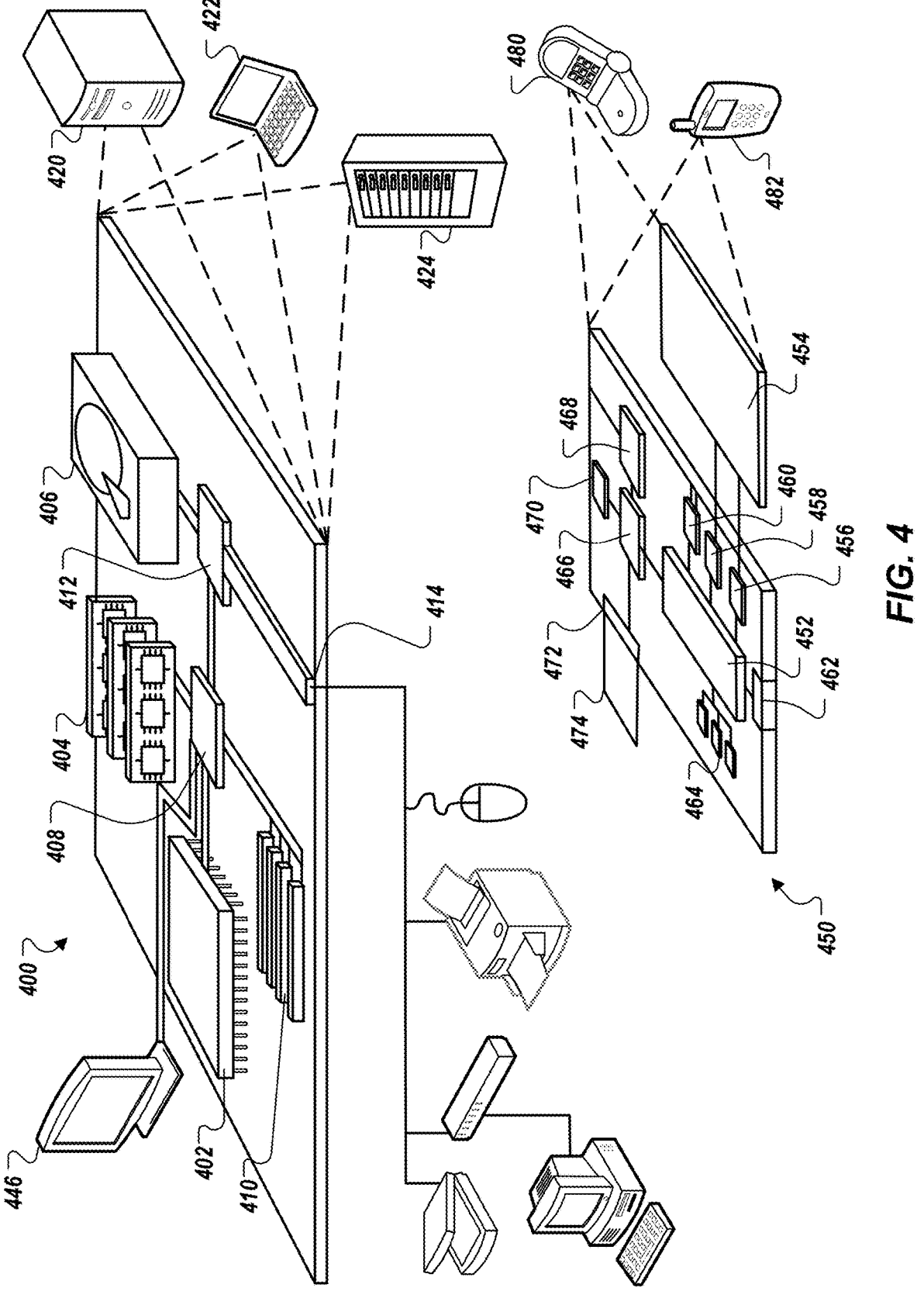
FIG. 4 shows a schematic diagram of an example computing system that can perform the methods described in the present disclosure.

FIG. 4 shows an example of a computing device 400 and an example of a mobile computing device that can be used to implement the techniques described here. For example, the backend system 112 in FIG. 1 can be in the form of the computing device 400, the mobile computing device 450, or a combination of them. The computing device 400 is intended to represent various forms of digital computers, such as laptops, desktops, workstations, personal digital assistants, servers, blade servers, mainframes, and other appropriate computers. The mobile computing device is intended to represent various forms of mobile devices, such as personal digital assistants, cellular telephones, smartphones, and other similar computing devices. The components shown here, their connections and relationships, and their functions, are meant to be exemplary only, and are not meant to limit implementations of the inventions described and/or claimed in this document.

The computing device 400 includes a processor 402, a memory 404, a storage device 406, a high-speed interface 408 connecting to the memory 404 and multiple high-speed expansion ports 410, and a low-speed interface 412 connecting to a low-speed expansion port 414 and the storage device 406. Each of the processor 402, the memory 404, the storage device 406, the high-speed interface 408, the high-speed expansion ports 410, and the low-speed interface 412, are interconnected using various busses, and can be mounted on a common motherboard or in other manners as appropriate. The processor 402 can process instructions for execution within the computing device 400, including instructions stored in the memory 404 or on the storage device 406 to display graphical information for a GUI on an external input/output device, such as a display 416 coupled to the high-speed interface 408. In other implementations, multiple processors and/or multiple buses can be used, as appropriate, along with multiple memories and types of memory. Also, multiple computing devices can be connected, with each device providing portions of the necessary operations (e.g., as a server bank, a group of blade servers, or a multi-processor system).

The memory 404 stores information within the computing device 400. In some implementations, the memory 404 is a volatile memory unit or units. In some implementations, the memory 404 is a non-volatile memory unit or units. The memory 404 can also be another form of computer-readable medium, such as a magnetic or optical disk.

The storage device 406 is capable of providing mass storage for the computing device 400. In some implementations, the storage device 406 can be or contain a computer-readable medium, such as a floppy disk device, a hard disk device, an optical disk device, or a tape device, a flash memory or other similar solid state memory device, or an array of devices, including devices in a storage area network or other configurations. A computer program product can be tangibly embodied in an information carrier. The computer program product can also contain instructions that, when executed, perform one or more methods, such as those described above. The computer program product can also be tangibly embodied in a computer- or machine-readable medium, such as the memory 404, the storage device 406, or memory on the processor 402.

The high-speed interface 408 manages bandwidth-intensive operations for the computing device 400, while the low-speed interface 412 manages lower bandwidth-intensive operations. Such allocation of functions is exemplary only. In some implementations, the high-speed interface 408 is coupled to the memory 404, the display 416 (e.g., through a graphics processor or accelerator), and to the high-speed expansion ports 410, which can accept various expansion cards (not shown). In the implementation, the low-speed interface 412 is coupled to the storage device 406 and the low-speed expansion port 414. The low-speed expansion port 414, which can include various communication ports (e.g., USB, Bluetooth, Ethernet, wireless Ethernet) can be coupled to one or more input/output devices, such as a keyboard, a pointing device, a scanner, or a networking device such as a switch or router, e.g., through a network adapter.

The computing device 400 can be implemented in a number of different forms, as shown in the figure. For example, it can be implemented as a standard server 420, or multiple times in a group of such servers. In addition, it can be implemented in a personal computer such as a laptop computer 422. It can also be implemented as part of a rack server system 424. Alternatively, components from the computing device 400 can be combined with other components in a mobile device (not shown), such as a mobile computing device 450. Each of such devices can contain one or more of the computing device 400 and the mobile computing device 450, and an entire system can be made up of multiple computing devices communicating with each other.

The mobile computing device 450 includes a processor 452, a memory 464, an input/output device such as a display 454, a communication interface 466, and a transceiver 468, among other components. The mobile computing device 450 can also be provided with a storage device, such as a micro-drive or other device, to provide additional storage. Each of the processor 452, the memory 464, the display 454, the communication interface 466, and the transceiver 468, are interconnected using various buses, and several of the components can be mounted on a common motherboard or in other manners as appropriate.

The processor 452 can execute instructions within the mobile computing device 450, including instructions stored in the memory 464. The processor 452 can be implemented as a chipset of chips that include separate and multiple analog and digital processors. The processor 452 can provide, for example, for coordination of the other components of the mobile computing device 450, such as control of patient interfaces, applications run by the mobile computing device 450, and wireless communication by the mobile computing device 450.

The processor 452 can communicate with a patient through a control interface 458 and a display interface 456 coupled to the display 454. The display 454 can be, for example, a TFT (Thin-Film-Transistor Liquid Crystal Display) display or an OLED (Organic Light Emitting Diode) display, or other appropriate display technology. The display interface 456 can comprise appropriate circuitry for driving the display 454 to present graphical and other information to a patient. The control interface 458 can receive commands from a patient and convert them for submission to the processor 452. In addition, an external interface 462 can provide communication with the processor 452, so as to enable near area communication of the mobile computing device 450 with other devices. The external interface 462 can provide, for example, for wired communication in some implementations, or for wireless communication in other implementations, and multiple interfaces can also be used.

The memory 464 stores information within the mobile computing device 450. The memory 464 can be implemented as one or more of a computer-readable medium or media, a volatile memory unit or units, or a non-volatile memory unit or units. An expansion memory 474 can also be provided and connected to the mobile computing device 450 through an expansion interface 472, which can include, for example, a SIMM (Single In Line Memory Module) card interface. The expansion memory 474 can provide extra storage space for the mobile computing device 450, or can also store applications or other information for the mobile computing device 450. Specifically, the expansion memory 474 can include instructions to carry out or supplement the processes described above, and can include secure information also. Thus, for example, the expansion memory 474 can be provide as a security module for the mobile computing device 450, and can be programmed with instructions that permit secure use of the mobile computing device 450. In addition, secure applications can be provided via the SIMM cards, along with additional information, such as placing identifying information on the SIMM card in a non-hackable manner.

The memory can include, for example, flash memory and/or NVRAM memory (non-volatile random access memory), as discussed below. In some implementations, a computer program product is tangibly embodied in an information carrier. The computer program product contains instructions that, when executed, perform one or more methods, such as those described above. The computer program product can be a computer- or machine-readable medium, such as the memory 464, the expansion memory 474, or memory on the processor 452. In some implementations, the computer program product can be received in a propagated signal, for example, over the transceiver 468 or the external interface 462.

The mobile computing device 450 can communicate wirelessly through the communication interface 466, which can include digital signal processing circuitry where necessary. The communication interface 466 can provide for communications under various modes or protocols, such as GSM voice calls (Global System for Mobile communications), SMS (Short Message Service), EMS (Enhanced Messaging Service), or MMS messaging (Multimedia Messaging Service), CDMA (code division multiple access), TDMA (time division multiple access), PDC (Personal Digital Cellular), WCDMA (Wideband Code Division Multiple Access), CDMA2000, or GPRS (General Packet Radio Service), among others. Such communication can occur, for example, through the transceiver 468 using a radio-frequency. In addition, short-range communication can occur, such as using a Bluetooth, WiFi, or other such transceiver (not shown). In addition, a GPS (Global Positioning System) receiver module 470 can provide additional navigation- and location-related wireless data to the mobile computing device 450, which can be used as appropriate by applications running on the mobile computing device 450.

The mobile computing device 450 can also communicate audibly using an audio codec 460, which can receive spoken information from a patient and convert it to usable digital information. The audio codec 460 can likewise generate audible sound for a patient, such as through a speaker, e.g., in a handset of the mobile computing device 450. Such sound can include sound from voice telephone calls, can include recorded sound (e.g., voice messages, music files, etc.) and can also include sound generated by applications operating on the mobile computing device 450.

The mobile computing device 450 can be implemented in a number of different forms, as shown in the figure. For example, it can be implemented as a cellular telephone 480. It can also be implemented as part of a smart-phone 482, personal digital assistant, or other similar mobile device.

Various implementations of the systems and techniques described here can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms machine-readable medium and computer-readable medium refer to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term machine-readable signal refers to any signal used to provide machine instructions and/or data to a programmable processor.

To provide for interaction with a patient, the systems and techniques described here can be implemented on a computer having a display device (e.g., a CRT (cathode ray tube) or LCD (liquid crystal display) monitor) for displaying information to the patient and a keyboard and a pointing device (e.g., a mouse or a trackball) by which the patient can provide input to the computer. Other kinds of devices can be used to provide for interaction with a patient as well; for example, feedback provided to the patient can be any form of sensory feedback (e.g., visual feedback, auditory feedback, or tactile feedback); and input from the patient can be received in any form, including acoustic, speech, or tactile input.

The systems and techniques described here can be implemented in a computing system that includes a back end component (e.g., as a data server), or that includes a middleware component (e.g., an application server), or that includes a front end component (e.g., a client computer having a graphical patient interface or a Web browser through which a patient can interact with an implementation of the systems and techniques described here), or any combination of such back end, middleware, or front end components. The components of the system can be interconnected by any form or medium of digital data communication (e.g., a communication network). Examples of communication networks include a local area network (LAN), a wide area network (WAN), and the Internet.

The computing system can include clients and servers. A client and server are generally remote from each other and typically interact through a communication network. The relationship of client and server arises by virtue of computer programs running on the respective computers and having a client-server relationship to each other.

A number of implementations of the present disclosure have been described. Nevertheless, it will be understood that various modifications may be made without departing from the spirit and scope of the present disclosure. Accordingly, other implementations are within the scope of the following claims.

What is claimed is:

1. A computer-implemented method comprising:
   receiving, by a computing system, one or more biomarker baselines for a patient, the biomarker baselines representing biological characteristics of the patient before going through a medical treatment;
   receiving, by the computing system and from a client device, one or more signals representing respective biomarkers of the patient measured over a period of time subsequent to starting the medical treatment, wherein the signals are generated by one or more wearable sensors that are worn by the patient to measure the respective biomarkers over the period of time;
   analyzing, by the computing system, the signals to obtain the respective biomarkers, wherein the analyzing comprises:
      applying AI models on the one or more signals to obtain the respective biomarkers by estimating biomarkers based on patterns detected in the one or more signals over the period of time, wherein at least one of the AI models comprises an algorithm to determine (i) a left step or a right step of the patient and (ii) a step duration of the left step or the right step based on the one or more signals;
   determining efficacy of the medical treatment by comparing each of the obtained biomarkers with one or more respective biomarker baselines to determine respective changes in the biomarkers, and
      comparing the respective changes with respective threshold values to determine the efficacy of the medical treatment on the patient; and
   storing the determined efficacy for the medical treatment.

2. The method of claim 1, wherein the respective biomarkers comprise two or more of sleep apnea, gait, or physical activity.

3. The method of claim 1, wherein at least one signal includes data measured continuously over hours each day during the period of time.

4. The method of claim 1, wherein the medical treatment is a treatment for pediatric achondroplasia patients.

5. The method of claim 1, wherein the medical treatment comprises consuming a drug.

6. The method of claim 5, further comprising:
   receiving respective measurement signals from multiple client devices respectively worn by multiple patients;
   determining respective biomarkers for each of the multiple patients based on the respective measurement signals;
   determining one or more dosages of the drug that causes the most changes in the respective biomarkers in at least some of the multiple patients;
   determining, from among the one or more dosages, a particular dosage that causes the most changes in the respective biomarkers on most of patients in the multiple patients; and
   storing or reporting the particular dosage as a recommended dosage for the drug.

7. The method of claim 1, wherein the respective biomarkers include sleep apnea,
   wherein the method further comprises calculating an apnea hypopnea index based on the received signals, and
   wherein determining the efficacy of the medical treatment further comprises;
      determining a change in the apnea hypopnea index, and
      marking the medical treatment as effective in response to determining a decrease in the apnea hypopnea index for more than a particular threshold value.

8. The method of claim 1, wherein the respective biomarkers include gait or physical activity assessments that are measured based on one or more of gait speed, step length, step duration, or physical activity measure of the patient.

9. The method of claim 1, wherein analyzing the signals further comprises:
   filtering each signal in the received signals to cleanse the signal for a particular range of frequencies to generate a respective cleansed signal,
   wherein the AI models are applied on the respective cleansed signal.

10. The method of claim 1, wherein the client device is remote from the computing system, and the signals are received from the client device through one or more wireless communication links.

11. The method of claim 1, wherein the client device includes at least one sensor in the one or more wearable sensors.

12. The method of claim 1, further comprising modulating the medical treatment based on the determined efficacy.

13. A system comprising:
   one or more computers; and
   one or more computer-readable storage devices storing instructions that are operable, when executed by the one or more computers, to cause the one or more computers to perform operations comprising:

receiving, one or more biomarker baselines for a patient, the biomarker baselines representing biological characteristics of the patient before going through a medical treatment;

receiving, from a client device, one or more signals representing respective biomarkers of the patient measured over a period of time subsequent to starting the medical treatment, wherein the signals are generated by one or more wearable sensors that are worn by the patient to measure the respective biomarkers over the period of time;

analyzing the signals to obtain the respective biomarkers, wherein the analyzing comprises:

applying AI models on the one or more signals to obtain the respective biomarkers by estimating biomarkers based on patterns detected in the one or more signals over the period of time, wherein at least one of the AI models comprises an algorithm to determine (i) a left step or a right step of the patient and (ii) a step duration of the left step or the right step based on the one or more signals;

determining efficacy of the medical treatment by comparing each of the obtained biomarkers with one or more respective biomarker baselines to determine respective changes in the biomarkers, and comparing the respective changes with respective threshold values to determine the efficacy of the medical treatment on the patient; and storing the determined efficacy for the medical treatment.

14. The system of claim 13, wherein the client device is remote from the system, and the signals are received from the client device through one or more wireless communication links.

15. The system of claim 13, wherein the respective biomarkers comprise two or more of sleep apnea, gait, or physical activity.

16. The system of claim 13, wherein the medical treatment comprises consuming a drug, and the operations further comprise;

receiving respective measurement signals from multiple client devices respectively worn by multiple patients;

determining respective biomarkers for each of the multiple patients based on the respective measurement signals;

determining one or more dosages of the drug that causes the most changes in the respective biomarkers in each at least some of the multiple patients;

determining, from among the one or more dosages, a particular dosage that causes the most changes in the respective biomarkers on most of patients in the multiple patients; and storing or reporting the particular dosage as a recommended dosage for the drug.

17. A non-transitory, computer-readable medium storing one or more instructions that are executable by one or more computers and that when executed by the one or more computers cause the one or more computers to perform operations comprising:

receiving, one or more biomarker baselines for a patient, the biomarker baselines representing biological characteristics of the patient before going through a medical treatment;

receiving, from a client device, one or more signals representing respective biomarkers of the patient measured over a period of time subsequent to starting the medical treatment, wherein the signals are generated by one or more wearable sensors that are worn by the patient to measure the respective biomarkers over the period of time;

analyzing the signals to obtain the respective biomarkers, wherein the analyzing comprises:

applying AI models on the one or more signals to obtain the respective biomarkers by estimating biomarkers based on patterns detected in the one or more signals over the period of time, wherein at least one of the AI models comprises an algorithm to determine (i) a left step or a right step of the patient and (ii) a step duration of the left step or the right step based on the one or more signals;

determining efficacy of the medical treatment by comparing each of the obtained biomarkers with one or more respective biomarker baselines to determine respective changes in the biomarkers, and comparing the respective changes with respective threshold values to determine the efficacy of the medical treatment on the patient; and storing the determined efficacy for the medical treatment.

18. The non-transitory, computer-readable medium of claim 17, wherein the respective biomarkers comprise two or more of sleep apnea, gait, or physical activity.

19. The non-transitory, computer-readable medium of claim 17, wherein the medical treatment comprises consuming a drug, and the operations further comprise:

receiving respective measurement signals from multiple client devices respectively worn by multiple patients;

determining respective biomarkers for each of the multiple patients based on the respective measurement signals;

determining one or more dosages of the drug that causes the most changes in the respective biomarkers in each at least some of the multiple patients;

determining, from among the one or more dosages, a particular dosage that causes the most changes in the respective biomarkers on most of patients in the multiple patients; and storing or reporting the particular dosage as a recommended dosage for the drug.

20. The non-transitory, computer-readable medium of claim 17, wherein analyzing the signals further comprises filtering each signal in the received signals to cleanse the signal for a particular range of frequencies to generate respective cleansed signals, wherein the AI models are applied on the respective cleansed signal.

\* \* \* \* \*